US010687889B2

(12) United States Patent
Amit

(10) Patent No.: US 10,687,889 B2
(45) Date of Patent: Jun. 23, 2020

(54) PATIENT-SPECIFIC PRE-SHAPED CARDIAC CATHETER

(71) Applicant: BIOSENSE WEBSTER (ISRAEL) LTD., Yokneam (IL)

(72) Inventor: Matityahu Amit, Zur-Yagal (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 149 days.

(21) Appl. No.: 14/051,491

(22) Filed: Oct. 11, 2013

(65) Prior Publication Data

US 2015/0105770 A1   Apr. 16, 2015

(51) Int. Cl.
*A61B 18/14* (2006.01)
*A61B 18/00* (2006.01)
*A61B 17/00* (2006.01)
*A61B 34/10* (2016.01)

(52) U.S. Cl.
CPC .............. *A61B 18/1492* (2013.01); *A61B 2017/00867* (2013.01); *A61B 2018/0016* (2013.01); *A61B 2018/0022* (2013.01); *A61B 2018/00267* (2013.01); *A61B 2018/00577* (2013.01); *A61B 2018/1435* (2013.01); *A61B 2018/1467* (2013.01); *A61B 2034/105* (2016.02); *Y10T 29/49* (2015.01); *Y10T 29/49117* (2015.01)

(58) Field of Classification Search
CPC .. A61B 2018/00285; A61B 2018/1405; A61B 2018/00351; A61B 2019/501; A61B 2019/504; A61B 2019/508; G09B 23/285; G09B 23/30
See application file for complete search history.

(56) References Cited

U.S. PATENT DOCUMENTS

| | | | |
|---|---|---|---|
| 4,591,341 A * | 5/1986 | Andrews | ............. 433/6 |
| 5,391,199 A | 2/1995 | Ben Haim | |
| 5,549,661 A | 8/1996 | Kordis et al. | |
| 5,617,854 A | 4/1997 | Munsif | |
| 5,944,022 A | 8/1999 | Nardella | |
| 5,983,126 A | 11/1999 | Wittkampf | |
| 6,239,724 B1 | 5/2001 | Doron | |
| 6,332,089 B1 | 12/2001 | Acker | |
| 6,456,864 B1 | 9/2002 | Swanson | |
| 6,484,118 B1 | 11/2002 | Govari | |

(Continued)

FOREIGN PATENT DOCUMENTS

| | | |
|---|---|---|
| CN | 101309651 A | 11/2008 |
| WO | WO 96/05768 A1 | 2/1996 |

(Continued)

OTHER PUBLICATIONS

Mathias Markert, Stefun Weber, Tim C. Lueth. A beating heart model 3D printed from specific patient data. Aug. 23-25, 2007. Proceeding of the 29th Annual International Conference of the IEEE EMBS, pp. 4472-4475.*

(Continued)

*Primary Examiner* — Michael F Peffley
*Assistant Examiner* — Bo Ouyang

(57) ABSTRACT

A method includes receiving one or more images of an organ of a patient. A physical model of at least a target region of the organ is manufactured based on the images. A distal tip of a medical probe is pre-shaped to fit a surface of the physical model corresponding to the target region.

6 Claims, 4 Drawing Sheets

(56) References Cited

U.S. PATENT DOCUMENTS

| | | |
|---|---|---|
| 6,618,612 B1 | 9/2003 | Acker |
| 6,690,963 B2 | 2/2004 | Ben Haim |
| 2002/0065455 A1 | 5/2002 | Ben Haim |
| 2003/0009095 A1* | 1/2003 | Skarda .......................... 600/374 |
| 2003/0023266 A1* | 1/2003 | Borillo ............. A61B 17/12022 606/200 |
| 2003/0120150 A1 | 6/2003 | Govari |
| 2004/0068178 A1 | 4/2004 | Govari |
| 2007/0049924 A1* | 3/2007 | Rahn .............................. 606/41 |
| 2007/0083194 A1* | 4/2007 | Kunis et al. ................... 606/41 |
| 2007/0270943 A1 | 11/2007 | Solem et al. |
| 2009/0216221 A1* | 8/2009 | Davis ................. A61B 18/1492 606/33 |
| 2010/0076426 A1* | 3/2010 | de la Rama ....... A61B 18/1492 606/41 |
| 2010/0256606 A1 | 10/2010 | Lippert et al. |
| 2011/0118726 A1* | 5/2011 | De La Rama et al. ......... 606/33 |

FOREIGN PATENT DOCUMENTS

| | | |
|---|---|---|
| WO | WO 2009/094588 A2 | 7/2009 |
| WO | WO 2013/025814 A1 | 2/2013 |

OTHER PUBLICATIONS

EP Search Report EP 14 18 8445 dated Feb. 2015.
Markert et al. A Beating Heart Model 3D Printed From Specific Patient Data. Proceedings of the 29$^{th}$ Annual International Conference of the IEEE EMBS, France (2007) 4472-4475.

\* cited by examiner

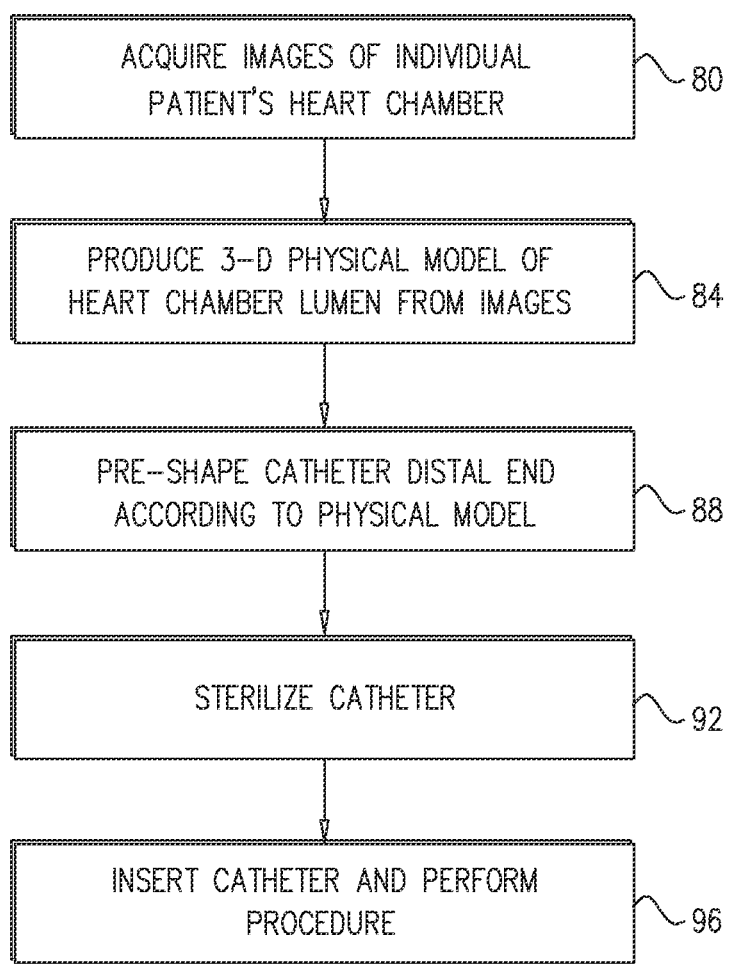

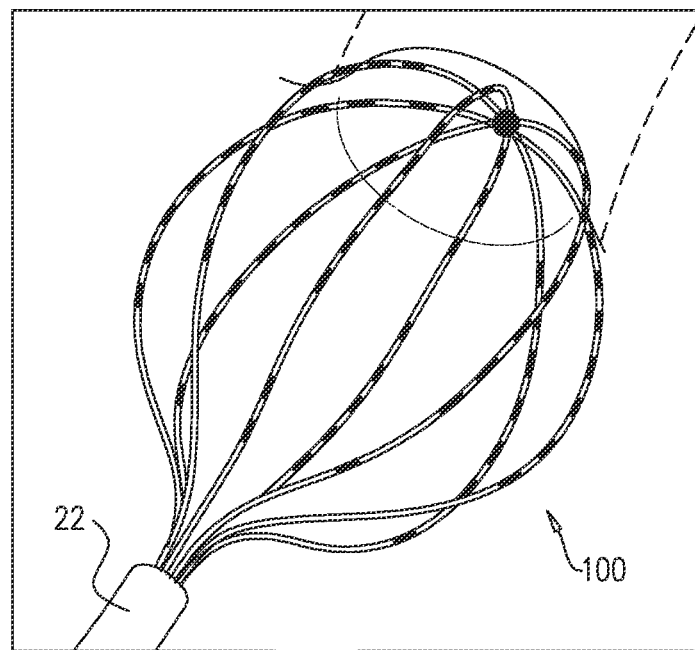
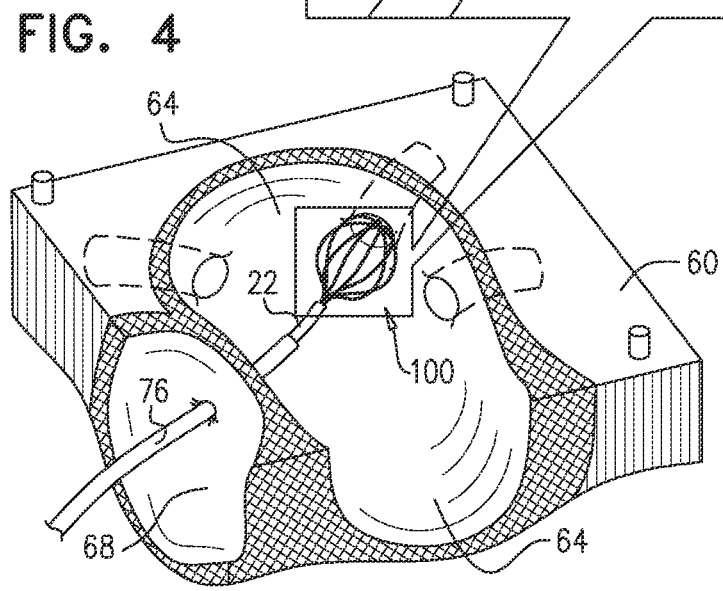
FIG. 4

PATIENT-SPECIFIC PRE-SHAPED CARDIAC CATHETER

FIELD OF THE INVENTION

The present invention relates generally to medical devices, and particularly to pre-shaped medical probes.

BACKGROUND OF THE INVENTION

Invasive probes are used in a variety of medical procedures, such as cardiac electrophysiological (EP) mapping and ablation. Some probes have tips that are pre-shaped to the desired form. For example, U.S. Pat. No. 5,617,854, whose disclosure is incorporated herein by reference, describes a pre-shaped cardiac catheter for mapping and selective ablation of a portion of cardiac circuitry. The catheter includes a pre-shaped first curved portion for positioning around the ostium of coronary sinus and a second curved portion for maintaining the first curved portion in its desired position. A catheter assembly, including a guide-wire and a preshaped catheter, is inserted to a location proximal the atrium. As the guide-wire is withdrawn from within the catheter, the catheter assumes its preshaped form at the target location. Alternatively, a catheter assembly, with or without a guide-wire, may be introduced to the target ablation site via a catheter sheath. The catheter includes an array of spaced apart electrodes on at least a portion of the catheter.

U.S. Patent Application Publication 2007/0049924, whose disclosure is incorporated herein by reference, describes an ablation catheter for setting a lesion. The catheter contains an ablation element that can be slid out of a catheter sleeve and has a looped section which, when the element is slid out, self-expands into an automatically or manually imposed pre-specified shape corresponding to the actual shape of the area of tissue requiring to be ablated.

SUMMARY OF THE INVENTION

An embodiment of the present invention that is described herein provides a method including receiving one or more images of an organ of a patient. A physical model of at least a target region of the organ is manufactured based on the images. A distal tip of a medical probe is pre-shaped to fit a surface of the physical model corresponding to the target region.

In some embodiments, the method includes inserting the medical probe having the pre-shaped distal tip into the organ of the patient, and applying a medical procedure to the target region of the organ using the probe. In some embodiments, the organ includes a heart and the probe includes a cardiac catheter.

In a disclosed embodiment, the distal tip includes a shape-memory material that is configurable into shape by applying predefined operating conditions to the distal tip, and pre-shaping the distal tip includes fitting the distal tip to the surface of the physical model while the distal tip is subjected to the predefined operating conditions.

In some embodiments, the distal tip includes multiple electrodes and is extendable, when placed in the organ, to assume a three-dimensional shape, and pre-shaping the distal tip includes causing the multiple electrodes to make simultaneous physical contact with the target region. In an example embodiment, the distal tip includes a spiral having the electrodes disposed thereon. In another embodiment, the distal tip includes an extendable and collapsible basket having the electrodes disposed thereon.

In another embodiment, manufacturing the physical model includes printing the model using a three-dimensional (3-D) printer. In yet another embodiment, the distal tip of the medical probe is extendible to conform to the target region of the organ using an inflatable balloon.

There is additionally provided, in accordance with an embodiment of the present invention, a medical probe including an elongated tube and a distal tip. The elongated tube is configured for insertion into an organ of a patient. The distal tip is connected to the elongated tube and is pre-shaped, before the insertion, to conform to a target region of the organ by fitting the distal tip to the surface of a physical model of at least part of the organ.

The present invention will be more fully understood from the following detailed description of the embodiments thereof, taken together with the drawings in which:

BRIEF DESCRIPTION OF THE DRAWINGS

FIG. 3 is a flow chart that schematically illustrates a method for pre-shaping and using a cardiac catheter, in accordance with an embodiment of the present invention; and FIG. 4 is a schematic illustration of catheter pre-shaping using a physical model, in accordance with an alternative embodiment of the present invention.

DETAILED DESCRIPTION OF EMBODIMENTS

Overview

In some medical procedures, such as cardiac ablation and EP mapping, one or more electrodes on the distal tip of a medical probe are put in contact with the surface of a target region in an organ. Proper contact with the surface of the organ is important for the success of the procedure. In some types of catheters, the tip comprises multiple electrodes that should touch multiple points on the surface simultaneously.

In practice, however, the three-dimensional (3-D) shape of the organ surface changes from one patient to another. Heart chambers for example, and particularly the left atrium (LA), exhibit significant patient-to-patient variations in shape. Therefore, any single shape of the catheter tip will necessarily be a compromise that may degrade the quality of the procedure.

Embodiments of the present invention that are described herein provide improved techniques for producing and using medical probes. In these techniques, the tip of a medical probe is pre-shaped to match the actual 3-D shape of the target region of the organ surface of a specific patient. The medical procedure is then performed using the probe with the personalized pre-shaped tip. As a result, the contact quality between the probe electrodes and the organ surface is enhanced considerably. The embodiments described herein refer mainly to procedures performed in the heart using cardiac catheters, but the disclosed techniques can be used with various other types of medical probes for use in various other organs.

In some embodiments, the catheter tip is pre-shaped using a physical model of at least part of a cardiac chamber of the specific patient in question. The physical model is manufactured based on pre-acquired three-dimensional (3-D) images of the patient heart, e.g., CT or MRI images. The model may be produced, for example, using a 3-D printer.

The disclosed techniques can be used with various types of catheter tips, such as a collapsible basket tip that is inflated using a balloon, or a spiral tip. In some embodiments, the catheter tip comprises a flexible shape-memory material that can be formed into a desired shape and then fixed in that shape. Forming into shape can be performed, for example, by subjecting the tip to a certain temperature range. In order to match the specific surface shape, the catheter tip is pressed or otherwise fitted against the appropriate region of the physical model, and its shape is then fixed. The resulting catheter is typically sterilized and then used for performing the medical procedure, e.g., mapping or ablation.

When using the disclosed pre-shaping techniques, the catheter tip closely matches the actual 3-D shape of the desired region of the patient's inner heart surface. Therefore, the multiple electrodes on the catheter tip can achieve high-quality simultaneous contact with the heart surface. The quality of procedures such as EP mapping and ablation can therefore be improved considerably when using these techniques.

System Description

Figure 1:
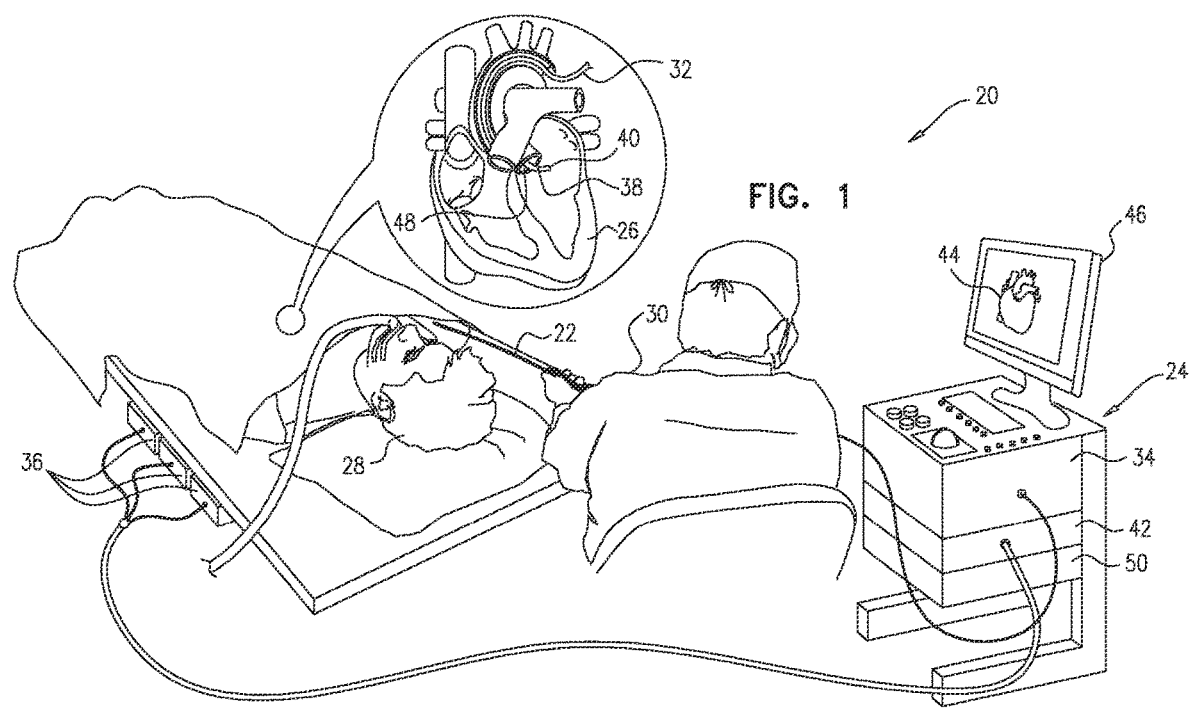
FIG. 1 is a block diagram that schematically illustrates a system for cardiac ablation, in accordance with an embodiment of the present invention.

FIG. 1 is a block diagram that schematically illustrates a system 20 for cardiac ablation, in accordance with an embodiment of the present invention. System 20 comprises a probe 22, in the preset example a cardiac catheter, and a control console 24. In the embodiment described herein, it is assumed by way of example that probe 22 may be used for ablation of tissue in a heart 26 of a patient 28 in order to treat cardiac arrhythmias. Alternatively or additionally, probe 22 may be used for other therapeutic and/or diagnostic purposes, such as for mapping electrical potentials in the heart or in another body organ.

Console 24 comprises a processor 42, typically a general-purpose computer, with suitable front end and interface circuits for receiving signals from probe 22 and for controlling the other components of system 20 described herein. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor may be carried out by dedicated or programmable digital hardware components.

An operator 30, typically a physician, inserts probe 22 through the vascular system of patient 28 so that a distal end 38 of probe 22 enters a chamber of heart 26. System 20 typically uses magnetic position sensing to determine position coordinates of the distal end inside heart 26. In this case console 24 comprises a driver circuit 34, which drives magnetic field generators 36 placed at known positions external to patient 28, e.g., below the patient's torso.

A magnetic field sensor 40 within the distal end of the probe generates electrical position signals in response to the magnetic fields from the coils, thereby enabling processor 42 to determine the position, i.e., the location and typically also the orientation, of distal end 32 within the chamber. The magnetic field sensor (i.e., the position sensor) typically comprises one or more coils, usually three coils orthogonal to each other.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Although in the present example system 20 is assumed to measure the position of distal end 38 using magnetic-based sensors, embodiments of the present invention may use other position tracking techniques, for example, tracking systems based on impedance measurements. Impedance-based position tracking techniques are described, for example, in U.S. Pat. Nos. 5,983,126, 6,456,864 and 5,944,022, whose disclosures are also incorporated herein by reference. Other position tracking techniques, known to one having ordinary skill in the art, may be used to determine the position of the distal end 32.

In order to ablate the tissue of heart 26, operator manipulates probe 22 so that distal end 38 is at multiple locations on (or in close proximity to) the inner surface of the chamber. At each location, an electrode coupled to the distal end measures a certain physiological property (e.g., the local surface electrical potential). Processor 42 correlates the location measurements, derived from the position signals of sensor 40, and the electrical potential measurements. Thus, the system collects multiple map points, with each map point comprising a coordinate on the inner chamber surface and a respective physiological property measurement at this coordinate.

Processor 42 uses the coordinates of the map points to construct a simulated surface of the cardiac chamber in question. Processor 42 then combines the electrical potential measurements of the map points with the simulated surface to produce a map of the potentials overlaid on the simulated surface. Processor 42 displays an image 44 of the map to operator 30 on a display 46.

Patient-Specific Catheter Pre-Shaping

In some embodiments, the distal tip of catheter 22 comprises multiple electrodes that should touch the inner surface of a target region in heart 26 simultaneously. In order to achieve high-quality simultaneous contact, the 3-D shape of the catheter tip (and thus the loci of the multiple electrodes) should closely match the 3-D shape of the target region.

The heart surface shape, however, varies considerably from one patient to another. In order to overcome these variations, in some embodiments the catheter tip is pre-shaped before the procedure to match the actual 3-D shape of the target region of the specific patient in question. Pre-shaping is performed using a physical 3-D model of at least part of the heart.

Figure 2A:
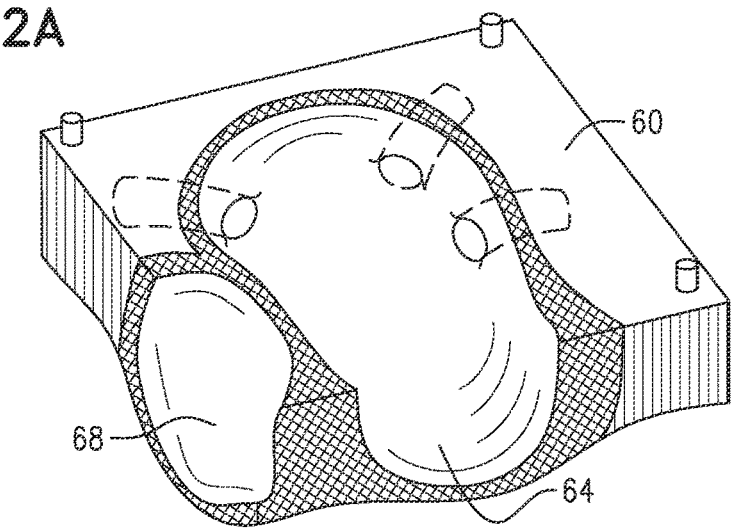
FIGS. 2A-2C are schematic illustrations of a process of pre-shaping a catheter, in accordance with an embodiment of the present invention.

FIG. 2A is a schematic illustration of a physical model 60 of part of heart 26 of patient 28, in accordance with an embodiment of the present invention. In the present example, model 60 represents a section 64 of the left atrium (LA) and a section 68 of the right atrium (RA) of heart 26. This model is used for pre-shaping catheter 22 for performing an ablation procedure in the LA.

Typically, model 60 is manufactured based on pre-acquired images of heart 26 or parts thereof. The images used for producing model 60 may comprise 2-D or 3-D images, and may comprise, for example, Computerized Tomography (CT) images, Magnetic Resonance Imaging (MRI) images, Ultrasound images and/or images of any other suitable modality or combination of modalities. In some embodiments, the 3-D heart shape images for manufacturing the model are obtained by mapping the inner heart surface using a catheter position tracking system such as the CARTO system described above.

Model 60 may be fabricated from any suitable material, such as a suitable plastic or polymer. In some embodiments, model 60 is printed using a 3-D printer. In a typical process, the pre-acquired images are processed by a suitable processor so as to calculate the 3-D shape of the heart surface. Physical model 60 is then produced from this 3-D shape, e.g., using a 3-D printer or other suitable means.

Model 60 aims to reconstruct the 3-D physical shape of the inner heart surface, at least in the target region of the medical procedure. Other surfaces and heart features may be omitted from the model. In the present example, model 60 reconstructs section 64 of the inner surface of the LA, including sections of the four pulmonary veins, plus section 68 of the RA.

An example physical model that can be used as model 60 is described by Markert et al., in "A Beating Heart Model 3D Printed from Specific Patient Data," Proceedings of the Annual Conference of the IEEE Engineering in Medicine and Biology Society, 2007, pages 4472-4475, which is incorporated herein by reference. Other examples of physical heart models are described in "Structural Heart Disease Modeling Project," University of Colorado, School of Medicine, Interventional Cardiology 3-D Lab, November, 2011, which is incorporated herein by reference. Alternatively, model 60 may have any other suitable shape and/or material composition, and it may be manufactures in any other suitable way.

Figure 2B:
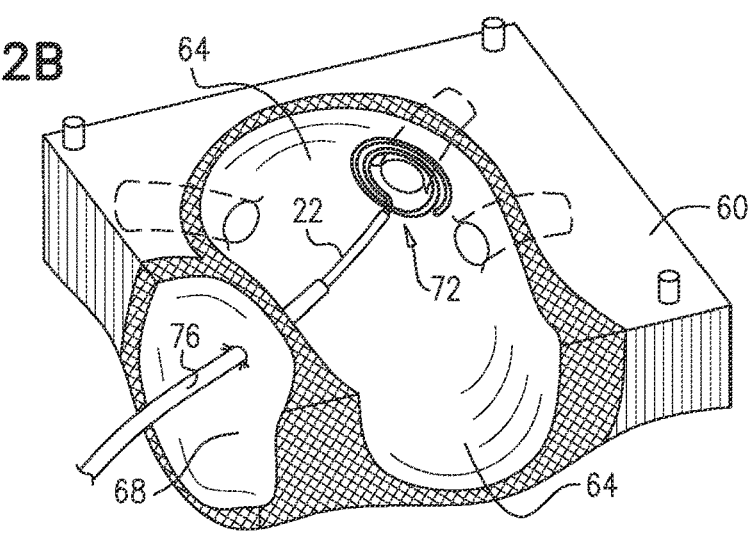

FIG. 2B is a schematic illustration of a process of pre-shaping catheter 22 using physical model 60, in accordance with an embodiment of the present invention. In the present example, catheter 22 comprises a distal tip 72 having a spiral shape. Multiple electrodes (not shown in the figure) are disposed along the spiral, for mapping and/or ablating multiple points around the ostium of one of the pulmonary veins. (An alternative embodiment in which the catheter tip comprises a collapsible "basket" is described further below.)

Tip 72 is made-up of, or at least comprises, a flexible shape-memory material, e.g., a Shape Memory Alloy (SMA). A shape-memory material can be set to a desired shape, and then permanently fixed at this shape, by applying a predefined operating condition. For example, SMAs such as copper-aluminum-nickel or nickel-titanium (NiTi) alloys can be fixed at a desired shape by shaping them while at a certain temperature range. Outside this temperature range the material is flexible but will return to the predefined shape when unconstrained.

Depending on the materials used, the temperature range may be, for example, in the range of 40-95° C. Generally, tip 72 may comprise any suitable shape-memory material that is shapeable using any suitable means.

As can be seen in the figure, catheter 22 is inserted via a sheath 76. Typically, sheath 76 is inserted via the vascular system until reaching the vicinity of the ablation site. Then, catheter 22 is inserted via the sheath until tip 72 extends from the sheath.

When using the flexible shape-memory material, sheath 76 forces tip 72 to assume a linear shape during insertion. When reaching the vicinity of the ablation site, tip 72 exits the sheath and re-assumes its spiral shape by virtue of the "memory" property of the shape-memory material.

Alternatively to using a sheath, catheter 22 may be guided to the ablation site by a guide wire. Such a guide wire is inserted via the vascular system until reaching the vicinity of the ablation site. Then, catheter 22 is inserted over the guide wire until reaching the desired position. In this implementation, the guide wire forces tip 72 to remain linear until reaching the ablation site. At the ablation site, the tip extends beyond the end of the guide wire and there re-assumes its predefined spiral shape.

The embodiments above refer to a spiral catheter tip. Alternatively, however, tip 72 may have any other suitable shape or configuration. One alternative example is a "basket" tip, which comprises an extensible mesh of SMA elements with electrodes disposed thereon. Any such tip can be used in the disclosed techniques.

In a typical pre-shaping process, which is shown in FIG. 2B, tip 72 is placed against the desired region in physical model 60. The placement of tip 72 imitates the desired tip position during the planned ablation procedure. The tip area (possibly including some or all of model 60) is heated to the temperature range needed for shaping the shape-memory material of the catheter tip. Tip 72 is then cooled, while pressed against the desired region in section 64 of the LA. As a result, tip assumes the 3-D shape of the inner surface of the patient LA. Tip 72 will retain this shape when removed from the model.

Figure 2C:
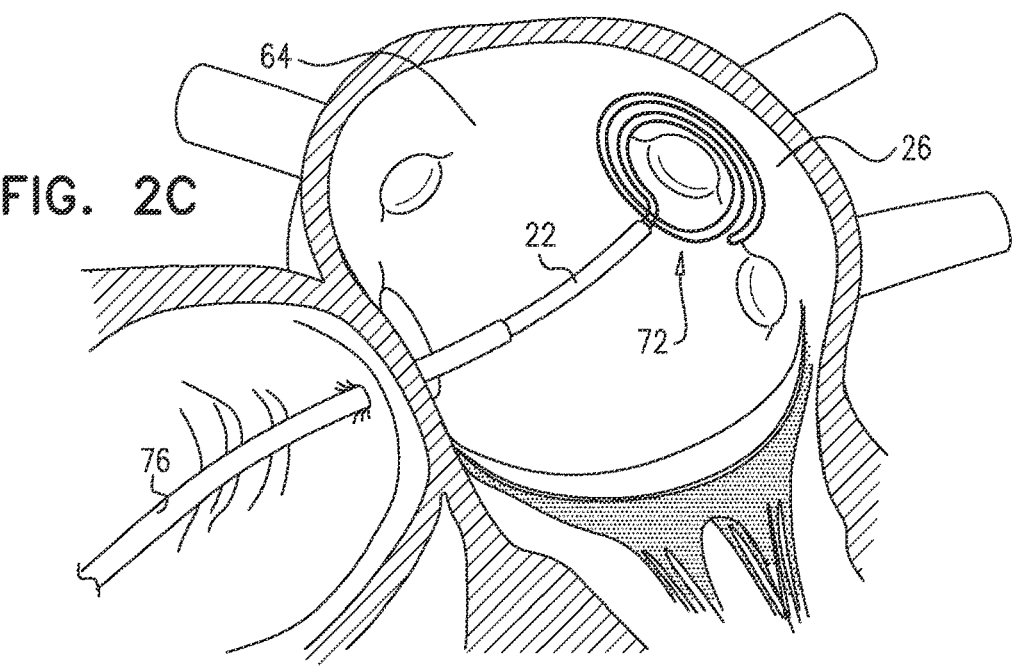

FIG. 2C is a schematic illustration of catheter 22 after insertion into heart 26 of patient 28, in accordance with an embodiment of the present invention. FIG. 2C shows sheath 76, with tip 72 of catheter 22 extending from the sheath and assuming the 3-D shaped fixed in model 60. Since model 60 closely matches the actual inner 3-D shape of the LA of heart 26, the electrodes in tip 72 are able to make simultaneous high-quality contact with multiple respective points on the LA surface.

FIG. 3 is a flow chart that schematically illustrates a method for pre-shaping and using a cardiac catheter, in accordance with an embodiment of the present invention. The method begins by acquiring one or more images of a heart chamber of patient 28 to be treated, at an imaging step 80. A 3-D physical model, such as model of FIG. 2A, is manufactured based on the acquired images, at a model fabrication step 84.

Distal tip 72 of catheter 22 is pre-shaped to match the 3-D shape of the desired region of the heart chamber, at a shaping step 88. Pre-shaping is performed by pressing tip 72 to the desired region in model 60, while the tip is subjected to the temperature used for shaping the shape-memory material. Catheter 22 is then sterilized, e.g., using Ethylene Oxide (EtO) sterilization, at a sterilization step 92. At this point the catheter is ready for use. At a procedure step 96, operator 30 performs the medical procedure (e.g., EP mapping or ablation) on patient 28 using the pre-shaped catheter tip.

FIG. 4 is a schematic illustration of catheter pre-shaping using a physical model, in accordance with an alternative embodiment of the present invention. In this embodiment, catheter 22 has a "basket" tip 100 that comprises a collapsible mesh of flexible arms. Multiple electrodes are fitted on the arms.

During a mapping procedure in the patient body, catheter 22 is inserted into the LA in its collapsed state—inside sheath 76. Catheter 22 is typically inserted via the Fossa Ovalis, and a balloon is inserted into the LA via the mitral valve using another catheter. The balloon is inserted into the mesh and inflated. As a result, the mesh of tip 100 extends and conforms to the inner surface of the LA, and the electrodes make high quality contact with the surface. FIG. 4 shows the process of pre-shaping this sort of catheter tip. As can be seen in the figure, tip 100 is inflated and pressed against the inner surface of model 60.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for manufacturing a patient-specific medical probe, comprising:
   a 3-D image of an organ of a patient;
   a medical probe comprising a distal tip, the distal tip comprising shape memory material configurable into a fixed desired shape by subjecting the distal tip to a known temperature range needed for shaping the shape memory material, and setting the shape by cooling the distal tip;
   a physical model derived from the 3-D image of the organ of the patient, the physical model having a desired target region in which other surfaces and features of the organ are omitted, the desired target region of the physical model having a configuration based on an identified region on a corresponding surface of the organ of the patient based on the 3-D image of the organ of the patient, the desired target region of the physical model configured for placement of the distal tip of the medical probe there against thereby defining a tip area of the physical model for which the distal tip can be shape set, the tip area of the physical model being configured to be heated to a temperature sufficient to allow the distal tip to be shape set;
   a heat source configured to heat the tip area of the physical model to a temperature needed for shaping the shape memory material of the distal tip, and the distal tip of the medical probe being further configured to assume a set 3-D shape of the identified region on the surface of the organ of the patient when cooled while pressed against the desired target region of the physical model.

2. The apparatus according to claim 1, wherein the organ comprises a heart, and wherein the probe comprises a cardiac catheter.

3. The apparatus according to claim 1, wherein the distal tip of the medical probe comprises multiple electrodes, the distal tip being extendable when placed in the organ of the patient to assume the 3-D shape, the distal tip being pre-shaped so as to cause the multiple electrodes to make simultaneous physical contact with the identified region on the surface of the organ of the patient.

4. The apparatus according to claim 1, wherein the distal tip comprises a spiral having the electrodes disposed thereon.

5. The apparatus according to claim 1, wherein the distal tip comprises an extendable and collapsible basket having the electrodes disposed thereon.

6. The apparatus according to claim 1, wherein the distal tip is extendible to conform to the identified region of the organ using an inflatable balloon.

* * * * *